United States Patent
Aaltonen et al.

(10) Patent No.: US 10,919,847 B2
(45) Date of Patent: Feb. 16, 2021

(54) PROCESS FOR THE PREPARATION OF ARYLSULFONYLPROPENENITRILES BY PHOTOCATALYTIC REACTIONS

(71) Applicant: Kemira Oyj, Helsinki (FI)

(72) Inventors: Toni Aaltonen, Espoo (FI); Oili Kallatsa, Turku (FI); Jaakko Simell, Helsinki (FI); Nina Sneitz, Helsinki (FI); Jonas Konn, Espoo (FI); Jaakko Hiltunen, Kauniainen (FI); Ari Koskinen, Helsinki (FI)

(73) Assignee: Kemira Oyj, Helsinki (FI)

( * ) Notice: Subject to any disclaimer, the term of this patent is extended or adjusted under 35 U.S.C. 154(b) by 0 days.

(21) Appl. No.: 16/642,385

(22) PCT Filed: Aug. 27, 2018

(86) PCT No.: PCT/FI2018/050604
§ 371 (c)(1),
(2) Date: Feb. 27, 2020

(87) PCT Pub. No.: WO2019/043289
PCT Pub. Date: Mar. 7, 2019

(65) Prior Publication Data
US 2020/0190026 A1   Jun. 18, 2020

(30) Foreign Application Priority Data
Aug. 29, 2017 (FI) ..................................... 20175768

(51) Int. Cl.
*C07C 315/04* (2006.01)
*C07C 317/32* (2006.01)

(52) U.S. Cl.
CPC .......... *C07C 315/04* (2013.01); *C07C 317/32* (2013.01)

(58) Field of Classification Search
CPC .............................. C07C 315/04; C07C 317/32
USPC ....................................................... 558/397
See application file for complete search history.

(56) References Cited

U.S. PATENT DOCUMENTS 3,541,119 A   11/1970   Richter et al.
4,049,695 A   9/1977    Burk et al.

FOREIGN PATENT DOCUMENTS

JP   2011231045 A   11/2011

OTHER PUBLICATIONS

Finnish Patent and Registration Office, Search report of 20175768 dated Mar. 29, 2018, 2 pages.
Najera, C. et al: Regio- and Stereo-selective Synthesis of β-Sulphonyl-α,β-Unsaturated Carbonyl Compounds via an Iodosulphonylation-Dehydroiodination Reaction. In: Journal of the Chemical Society, Perkin Transaction 1: Organic and Bio-Organic Chemistry Dec. 31, 1988, vol. 1988, pp. 1029-1032.
Da Silva Correa, C.M.M. et al: Reactions of the Free Toluene-p-sulphonyl Radical. Part I. Diagnostic Reactions of Free Radicals. In: Journal of the Chemical Society C: Organic Dec. 31, 1968, pp. 1874-1879.
Sawangphon, T. et al: An improved Synthesis of Vinyl- and β-Iodovinyl Sulfones by a Molecular Iodine-Mediated One-Pot Iodosulfonation-Dehydroiodination Reaction. In: Synthetic Communications Aug. 8, 2012, vol. 43, No. 12, pp. 1692-1707.
Katrun, P. et al: PhI(OAc)2/KI-Mediated Reaction of Aryl Sulfinates with Alkenes, Alkynes, and α,β-Unsaturated Carbonyl Compounds: Synthesis of Vinyl Sulfones and β-Iodovinyl Sulfones. In: Eur. J. Org. Chem. Dec. 31, 2010, pp. 5633-5641.
Harvey, I.W. et al: Free Radical Addition Reactions of Allylic Sulfones to Alkenes. In: Tetrahedron, May 5, 1997, vol. 53, No. 18, pp. 6493-6508.
Benedetti, F. et al: "Nucleophilic additions to alpha,beta-unsaturated sulphones. III", Gazzetta Chimica Italiana, vol. 117, XP950906, Jan. 1, 1987, pp. 391-394.
Adlington, Robert M. and Barrett, Anthony G.M.: "Sultone Formation from 2,4,6-Tri-isopropylbenzenesulphinic Acid", Journal of the Chemical Society, Perkin Transactions 1: Organic and Bio-Organic Chemistry, Jan. 1, 1980, pp. 1076-1079, XP9509062.
Whitmore F. et al: "The Reaction of Organic Mercury Compounds with Halides", Journal of the American Chemical Society, vol. 45, Jan. 1, 1923, pp. 1068-1071, XP002786240.
Hildebrand J. H. et al: "Solubility of Iodine in Ethyl Alcohol, Ethyl Ether, Mesitylene, p-Xylene, 2,2-Dimethylbutane, Cyclohexane and Perfluoro-n-heptane", JACS, vol. 72, No. 2, pp. 1017-1019, 1950.

*Primary Examiner* — Kristin A Vajda
(74) *Attorney, Agent, or Firm* — Berggren LLP

(57) ABSTRACT

A process for a preparation of arylsulfonylpropenenitriles is disclosed. A reaction starting from arylsulfonyl iodides is catalyzed by light. The process is scalable, environmentally benign and provides the product in good yield.

11 Claims, 3 Drawing Sheets

PROCESS FOR THE PREPARATION OF ARYLSULFONYLPROPENENITRILES BY PHOTOCATALYTIC REACTIONS

PRIORITY

This application is a U.S. national application of the international application number PCT/FI2018/050604 filed on Aug. 27, 2018 and claiming priority of Finnish application 20175768 filed on Aug. 29, 2017 the contents of all of which are incorporated herein by reference.

The present invention relates to a process for the preparation of arylsulfonylpropenenitriles by photocatalytic reactions from arylsulfonyl iodides. The process complies with the principles of green chemistry in order to facilitate a more environmentally benign manufacturing process for this class of compounds, is scalable and gives the products in good yields.

BACKGROUND

Compounds incorporating a vinylarenesulfonyl moiety have been found to be biologically interesting as potential neuroprotective agents against Parkinson's Disease, as antitrypanosomal agents against African sleeping sickness and as a means to combat Staphylococcus aureus by inhibition of a sortase SrtA isoform, just to name a few. Synthetically vinylarenesulfonyls are interesting due to their capability to act as Michael acceptors and due to their variety of cycloaddition reactions.

The applicant has also recently submitted an application disclosing several uses arylsulfonylpropenenitriles as biocides further adding to the interest in robust methods for the large scale synthesis of compounds of this type.

The known synthesis methods for these compounds generally suffer from one or more drawbacks limiting their utility in the large scale synthesis of the desired compounds. Among these drawbacks are low reactivity leading to poor yields and extended reaction times, expensive starting materials, complicated isolation procedures, and toxic, volatile, and/or flammable solvents used.

In order to make it possible to further explore the usefulness of the arylsulfonylpropenenitriles in many fields of application there is a need for a simple and cost-effective yet environmentally benign method suitable for the large-scale synthesis of these compounds.

SUMMARY OF THE INVENTION

According to the present invention, it was surprisingly found that arylsulfonylpropenenitriles can be readily synthesized from inexpensive sulfinates using a photocatalyzed radical reaction with a suitable vinylic compound such as acrylonitrile using propylene carbonate containing water as the solvent. No additional reagents such as metal catalysts are required in the process, thus markedly improving the overall atom economy as well as reducing the use of potentially environmentally harmful chemicals.

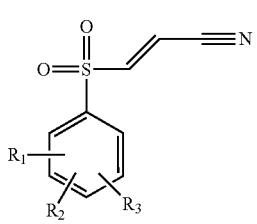

One aspect of the present invention is a process for the preparation of a compound according to general formula (I) from an arylsulfonyliodide by a photocatalyzed radical reaction with a suitable alkene wherein $R_1$, $R_2$ and $R_3$ independently represent a hydrogen atom; halogen atom; hydroxy group; amino group; alkylamino group; alkyl group; hydroxyalkyl group; haloalkyl group or alkoxy group having 1 to 4 carbon atoms; or an acylamido group having 1 to 10 carbon atoms. The intermediate formed in the radical reaction undergoes base-catalyzed elimination of an iodide to afford the target compound in good yields. The R-groups of the target compound can be varied according to the desired use of said compound(s).

DETAILED DESCRIPTION

Figure 1:
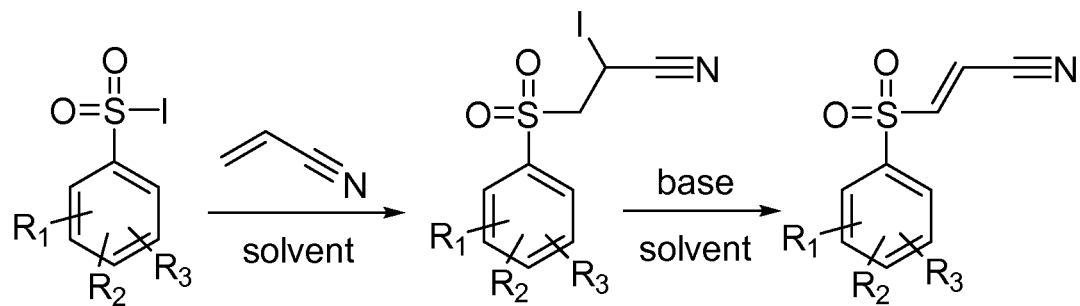
FIG. 1 presents a scheme of the reaction used for the synthesis of the arylsulfonyl propenenitriles.

As used herein, the expression visible light refers to electromagnetic radiation with a wavelength in the interval about 390 nm to about 700 nm.

A method for the preparation of arylsulfonylpropenenitriles is described herein. The method accomplishes the rapid conversion of the arylsulfonyliodide used as starting material to the desired arylsulfonylpropenenitrile. Optionally, the arylsulfonyliodide used in the reaction is synthesized separately or generated in situ. It has been surprisingly found that the reaction speed and conversion is greatly enhanced by the use of irradiation with visible light and the addition of water to the organic solvent used in the reaction.

Previously reported syntheses of vinylarenesulfonyl compounds all suffer from various drawbacks that limit the utility of these methods when scaling production to industrial scale.

One major problem arises from the use of solvents that are either banned from or not recommended for use for a number of reasons. The solvents used in previously published syntheses of vinylarenesulfonyl compounds include dichloromethane (environmentally harmful, volatile), diethyl ether (harmful, forms explosive peroxides, volatile, extremely flammable), N,N-dimethylformamide (toxic), ethyl acetate (harmful, volatile, flammable), and acetonitrile (slightly toxic, volatile, intermittent problems with availability, flammable, expensive).

In some cases, some of the starting materials used in known methods are either not available commercially in bulk and/or laboratory scale or are too expensive to make their use practical. Thus there was a need to develop a simple, economical, scalable, and environmentally benign method for the synthesis of vinylarenesulfonyl compounds.

In the present disclosure, we show that it is possible to efficiently synthesize arylsulfonylpropenenitriles of formula (I) from the corresponding iodides using photocatalysis. Compared to the traditional synthetic methods this leads to a short reaction time, no need for applying external heating, good conversions, an improved impurity profile, and the ability to use environmentally benign solvents.

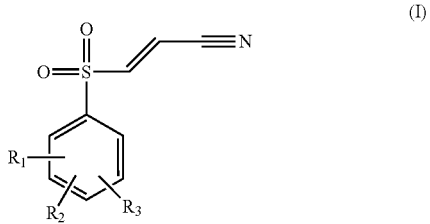

(I)

In one embodiment of the invention, $R_1$, $R_2$, and $R_3$ independently represent a hydrogen atom; a halogen atom; a hydroxy group; an amino group; an alkylamino group; an alkyl group; a hydroxyalkyl group; a haloalkyl group or an alkoxy group having 1 to 4 carbon atoms; or an acylamido group having 1 to 10 carbon atoms.

In another embodiment of the invention, $R_1$ represents a methyl group; an ethyl group, a propyl group; a butyl group; a methoxy group; an ethoxy group; a propoxy group; an isopropoxy group; a n-butoxy group; or a tertiary butoxy group; and $R_2$ and $R_3$ represent independently a hydrogen atom; a methyl group; an ethyl group, a propyl group; a butyl group; a methoxy group; an ethoxy group; a propoxy group; an isopropoxy group; a n-butoxy group; a tertiary butoxy group.

In a preferred embodiment of this invention $R_1$ represents a methyl group in the 4-position and $R_2$ and $R_3$ both represent hydrogen.

In one embodiment of the invention the organic solvent used is a polar aprotic solvent, preferably ethyl acetate, acetone, propylene carbonate, or 2-methyltetrahydrofuran, or any mixture thereof more preferably 2-methyltetrahydrofuran, propylene carbonate, or any mixture thereof and most preferably propylene carbonate.

In another preferred embodiment of this invention, the organic polar aprotic solvent used is propylene carbonate, to which water is added in an amount that is 0.1 to 20% (V/V), preferably 3 to 10% (V/V), most preferably 5% (V/V).

In one embodiment of the present invention the reaction is activated by irradiation with an external light source, preferably with visible light (approximately 390 to 700 nm).

The present invention enables completing the reaction with short reaction times. In one embodiment of the present invention the reaction time required for the formation of the arylsulfonylpropenenitriles compounds is less than 24 hours, preferably less than 4 hours, most preferably one hour or less.

The present invention enables completing the reaction at low reaction temperatures. In one embodiment of the present invention the reaction is performed at a temperature of 75° C. or less, preferably 50° C. or less, most preferably at a temperature from 0 to 25° C.

In one embodiment of the present invention the reaction is performed either in a batch reactor or a continuous flow reactor. The synthesis based on the methods disclosed herein may be employed either in a batch reactor or a continuous flow-type reactor. The use of a flow reactor setup adds the ability to irradiate the entire volume of the reaction mixture, further speeding up the conversion as compared to the batch-type reactor where only a small portion of the reaction mixture will be irradiated at any given point in time due to the limited penetration of the light into the solution. In order to at least partially overcome this limitation, a batch reactor requires intensive stirring of the reaction mixture.

In one embodiment of the reaction the elimination step is performed using a base, preferably selected from the group comprising inorganic or organic bases. In another embodiment the base is sodium bicarbonate, sodium hydroxide, sodium carbonate, triethylamine, trimethylamine, diethylamine, sodium acetate, piperidine, pyridine, or a mixture thereof, preferably triethylamine or sodium bicarbonate.

When compared to previously used methods, the radical reaction initiated by visible light produces a product mixture with an improved impurity profile, including a higher ratio of the (E) to (Z) isomers. This both simplifies the purification and improves the overall yield of the desired product. In one embodiment of the present invention the double bond present in the product is essentially in pure (E) orientation.

In one embodiment of the present invention the arylsulfonyliodide used is generated in situ effectively leading to a one-pot process for preparing the arylsulfonylpropenenitriles simplifying the overall production process.

The synthesis of the arylsulfonylpropenenitriles outlined in the reaction scheme presented in FIG. 1 comprises of two distinguishable reaction steps. The first step is the homolysis of the weak S—I bond in the arylsulfonyliodide to form an arylsulfonyl radical and an iodine radical followed by an attack by the arylsulfonyl-radical on the β-position of a vinylic compound. This first step is completed by the addition of the iodine radical to the vinylidenearylsulfonyl radical from the previous step yielding an iodide stable enough to be isolated, purified, and analyzed by conventional methods.

The reaction speed is improved significantly by irradiation with visible light to initiate the radical reaction; an added advantage is that the reaction also gives a higher final conversion when activated by light. A similar enhancement can also be achieved by the addition of a small amount of water to the reaction mixture.

The synthesis is completed by an elimination in which the previously formed iodide is treated with a suitable base to produce the desired arylsulfonylpropenenitrile. The base may be an organic or inorganic base such as sodium bicarbonate, sodium hydroxide, sodium carbonate, triethylamine, trimethylamine, diethylamine, sodium acetate, piperidine, pyridine, or a mixture thereof, preferably triethylamine or sodium bicarbonate.

In one embodiment of this invention the arylsulfonyliodide is prepared prior (e.g. 8 h prior) to the homolysis reaction to prevent decomposition of the arylsulfonyliodide. The arylsulfonyliodide can be prepared from the corresponding sodium arylsulfinate and elemental iodine in ethanol containing around 22% (w/w) water in a procedure modified from that published by F. Whitmore (in *JACS*, 1950, 72 (2), 1017-1020). The addition of ethanol aids in speeding up the reaction by transferring some of the iodine (which is generally soluble only in non-polar solvents) into the water phase and thus allowing it to react with the sulfinate salt (which is soluble only in water). Provided the amount of ethanol added is maintained as relatively low, the arylsulfonyliodide will precipitate out of the reaction mixture and can then be collected by a simple filtration. After filtering off the product, it may then be dried in high vacuum.

The iodide prepared in this fashion will decompose under the influence of daylight and atmospheric conditions and thus needs to be used as soon as possible in order to avoid contamination of the resulting reactions with decomposition products and/or unwanted byproducts.

In another embodiment of this invention the arylsulfonyliodide is prepared in situ effectively leading to a one-pot procedure for the synthesis of arylsulfonylpropylenenitriles. In this approach, the starting materials are mixed together in ethyl acetate (EtOAc) and refluxed. Upon cooling down the reaction mixture, a suitable base is added and the resulting mixture refluxed briefly. This allows for isolating the desired product after a washing procedure. The desired product (the (E)-alkene) can be crystallized from EtOAc/hexanes with the undesired (Z)-isomer remaining in the solution.

Experimental Section

The invention is described below with the help of examples. The examples are given only for illustrative purpose and they do not limit the scope of the invention.

Analytical Methods:

$^1$H- and $^{13}$C-NMR spectra were recorded on a Bruker Avance DPX400 system in $CDCl_3$.

HPLC analyses were performed on an Agilent 1100 series HPLC in reverse-phase mode with a Kinetex EVO C18 5 μm 4.6×150 mm column. The mobile phases used were 0.1% v/v $H_3PO_4$ in $H_2O$ and acetonitrile.

General Procedure for Screening of Reaction Conditions:

Screening reactions were performed using a Radley Carousel 12 Plus Reaction Station. Solvent (20 mL) was charged in a 40 mL tube followed by addition of acrylonitrile (5 mmol, 0.33 mL).

If specified: Water was added to the mixture (5 vol-% of the organic solvent).

Under constant stirring p-toluenesulfonyl iodide (1 eq.) was added. The reaction mixture was adjusted to the target temperature.

If specified: Irradiation of the mixture was carried out in accordance with the screening specification.

The reaction mixture was stirred for at least 24 h, unless otherwise stated, and monitored by taking periodic HPLC samples.

EXAMPLES

Example 1: One-Pot Pathway

Sodium p-toluenesulfinate (1.3 eq., 24.05 g) was suspended in EtOAc (300 mL). Acrylonitrile (100 mmol, 6.55 mL) and iodine (1.3 eq., 33.00 g) were added. The reaction mixture was refluxed for 1 h. The mixture was cooled down to 40° C. and NaOAc (1 eq., 8.20 g) was added. The mixture was refluxed for 15 min after which it was cooled to room temperature. The reaction was quenched by addition of $Na_2S_2O_3$ (0.1 eq., 450 mL). The organic phase was washed with saturated aqueous $NaHCO_3$ (100 mL) and brine (2×100 mL). The organic layer was dried over $Na_2SO_4$ and concentrated affording 8.65 g of a slightly yellow white solid (42%). The crude mixture was recrystallized from EtOAc and hexanes several times to afford 4.03 g (20%) of a white solid identified as the E-isomer of the target product. The Z-isomer was obtained by purifying the supernatant affording 0.61 g (3%) as a white solid.

(E)-3-(p-tolyl)sulfonylprop-2-enenitrile $^1$H NMR (400 MHz, $CDCl_3$, ppm) δ 7.81-7.75 (m, 2H), 7.44-7.37 (m, 2H), 7.21 (d, J=15.7 Hz, 1H), 6.51 (d, J=15.7 Hz, 1H), 2.48 (s, 3H). $^{13}$C NMR (101 MHz, $CDCl_3$, ppm) δ 149.36, 146.55, 134.22, 130.60, 128.59, 113.41, 110.12, 21.80.

(Z)-3-(p-tolyl)sulfonylprop-2-enenitrile $^1$H NMR (400 MHz, $CDCl_3$, ppm) δ 7.92-7.86 (m, 2H), 7.45-7.38 (m, 2H), 7.08 (d, J=11.3 Hz, 1H), 6.03 (d, J=11.3 Hz, 1H), 2.48 (s, 3H). $^{13}$C NMR (101 MHz, $CDCl_3$, ppm) δ 148.52, 146.58, 135.02, 130.42, 128.63, 111.99, 108.12, 21.82.

Comparative Example 1: Screening Organic Solvents for the One-Pot Reaction

Reactions were performed according to the general procedures for screening using ethyl acetate (EtOAc), propylene carbonate (PC), 2-methyltetrahydrofuran (Me-THF) and acetonitrile (MeCN) at 75° C. and the conversion of starting materials to products was followed by HPLC.

Figure 2:
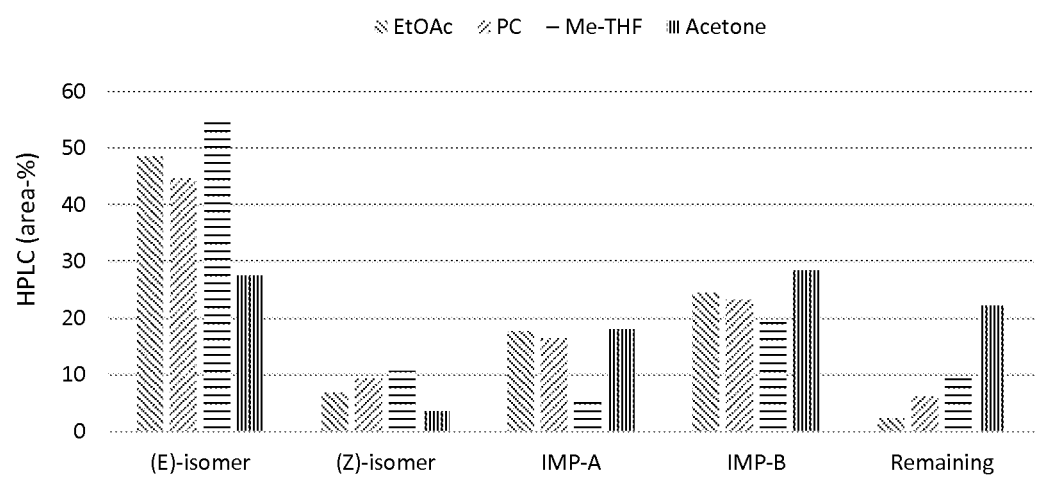
FIG. 2 presents the results from screening of the suitability of different solvents in the synthesis of arylsulfonylpropenenitriles in a one-pot procedure.

The results from the screening presented in FIG. 2 showed that the results were quite similar for EtOAc (48% conversion), PC (45%), and Me-THF (55%). Acetone was markedly worse that the other ones (37%).

Comparative Example 2: One-Pot Synthesis Using Water as a Solvent

Sodium p-toluenesulfinate (1.2 eq., 1.07 g) was dissolved in water (20 mL). Iodine (1.2 eq., 1.52 g) was added, nothing happened. Acrylonitrile (5 mmol, 0.33 mL) was added and the mixture was rapidly stirred at room temperature. The iodine dissolved gradually and yellow precipitate formed. The stirring was continued for 2 hours. A solution of $Na_2S_2O_3$ was added (10 w-%, 20 mL) and the mixture de-colorized. The precipitate was separated by filtration using a Buchner-funnel. The yellow solid was analyzed by $^1$H NMR revealing it to be p-toluenesulfinyl iodide.

Example 2: Screening Solvents for Synthesis of (E)-2-iodo-3-tosylpropanenitrile

The same solvents were screened as for the one-pot reaction. The reaction temperature used was 75° C. and the results analysed by HPLC.

Figure 3:
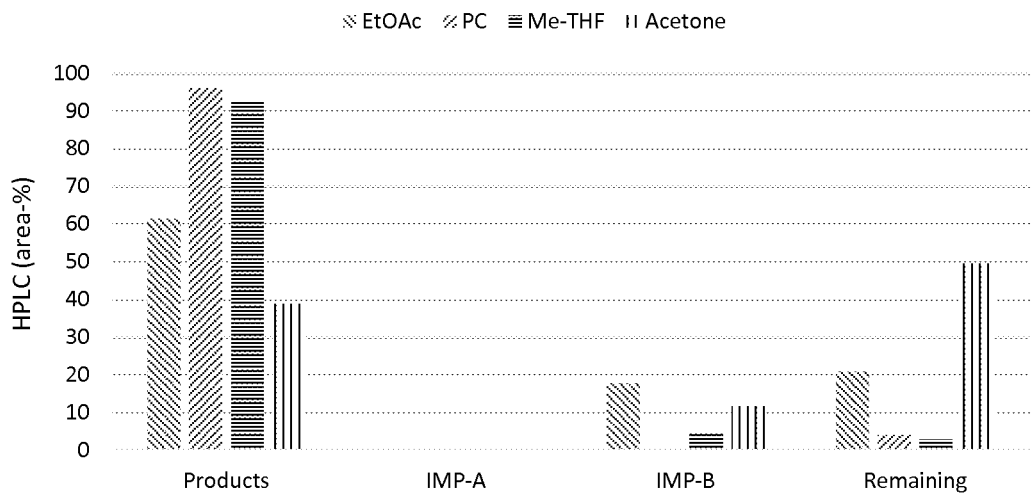
FIG. 3 presents the results from screening of the suitability of different solvents in the synthesis of (E)-2-iodo-3-tosylpropanenitrile.

The results of the solvent screening are presented in FIG. 3. In this screening, PC and Me-THF were found to be the best with conversions of approximately 93 and 88%, respectively. EtOAc and acetone showed significantly lower conversions (approximately 58 and 36%, respectively). It is also noteworthy that especially the reactions in PC and Me-THF showed significantly lower amounts of both (Z)-2-iodo-3-tosylpropanenitrile than the corresponding one-pot reactions.

Figure 4:
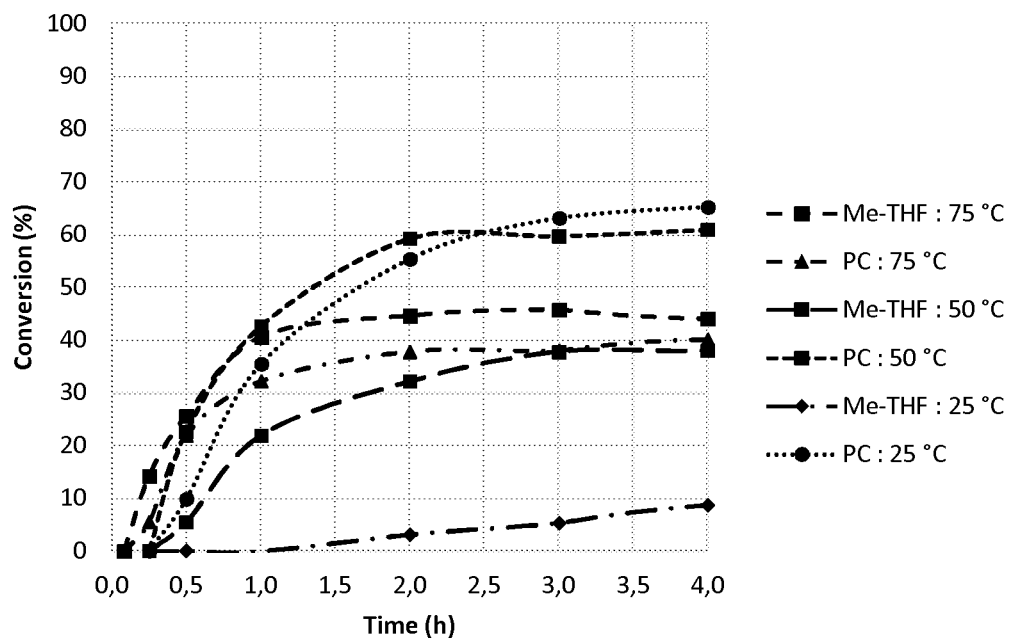
FIG. 4 presents the results from screening of the suitability of different solvents and reaction temperatures in the synthesis of (E)-2-iodo-3-tosylpropanenitrile.

Example 3: Screening Reaction Temperature for Synthesis of (E)-2-iodo-3-tosylpropanenitrile The effect of the reaction temperature on conversion and reaction speed was screened in PC and Me-THF (the two best solvents according to Comparative example 3) at 75, 50, and 25° C. The results from the screening of temperatures are summarized in FIG. 4.

Additionally, the reaction was investigated in PC at 5° C. which showed that the reaction was extremely slow at this temperature.

The screening of reaction temperatures shows that both reaction speed and final conversion are the highest when the reaction is performed at 25° C. in PC. The complete results of the screening are presented in FIG. 4.

Example 4: Screening the Effect of Moisture on the Synthesis of (E)-2-iodo-3-tosylpropanenitrile The effect of moisture on the reaction rate and total conversion was investigated by performing the reaction in completely dry conditions as well as with the addition of 5% (V/V) water to the solvent. For the experiment in dry conditions, the PC was dried over 4 Å molecular sieves prior to the reaction.

Figure 5:
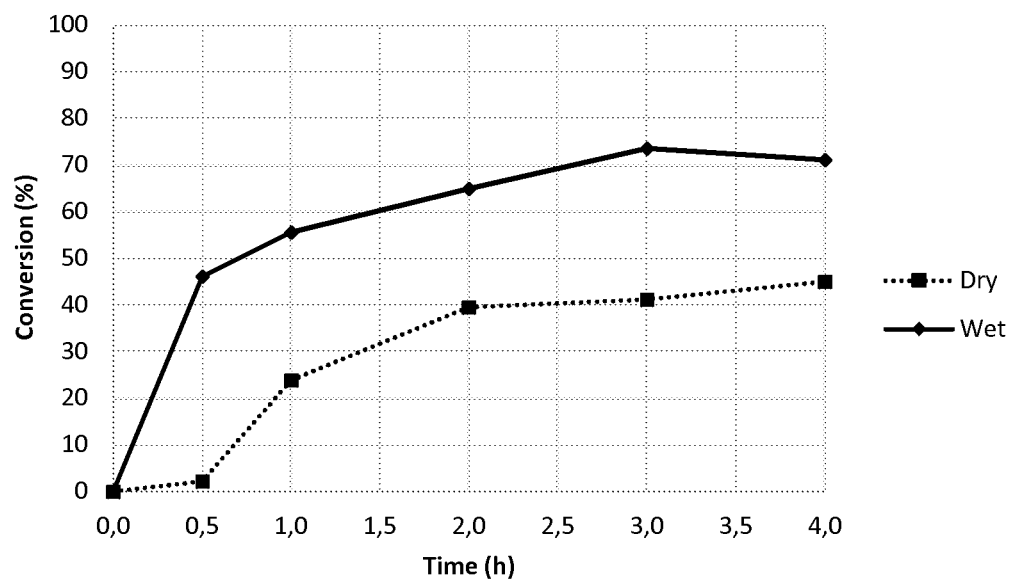
FIG. 5 presents the results from screening of the synthesis of (E)-2-iodo-3-tosylpropanenitrile in dry and wet conditions.

FIG. 5 shows the results of the dry and wet reactions. From these results it can be seen that the added moisture enhances both the reaction speed and the final conversion attained.

Example 5: Synthesis of (E)-2-iodo-3-tosylpropanenitrile Using Activation Light

In order to investigate the effect of light on the homolysis reaction, reaction conditions were screened in complete darkness, ambient light, and with visible light irradiation. All experiments were performed at 25° C. in propylene carbonate with 5% (V/V) added water.

Figure 6:
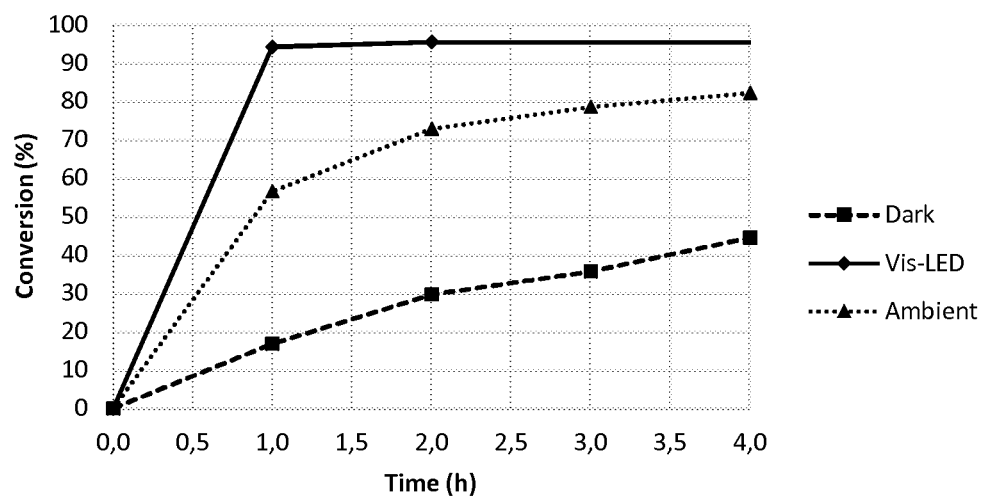
FIG. 6 presents the results from screening of the synthesis of (E)-2-iodo-3-tosylpropanenitrile in dark and ambient light conditions, and with irradiation with visible light.

FIG. 6 shows a clear advantage in using visible light irradiation to activate the reaction. When using visible light activation, the reaction reaches completion in approximately 1 h, ambient light conditions lead to a significantly slower reaction with darkness leading to quite sluggish reaction speeds.

Example 6: Synthesis of p-Toluenesulfonyl Iodide

Sodium p-toluenesulfinate (1.05 eq.) was dissolved in 250 mL of distilled water. A 50 mL solution of iodine (25 mmol) in ethanol was added slowly during 2 minutes to the vigorously stirred solution of sodium p-toluenesulfinate. A precipitate started forming immediately upon addition. The resulting slurry was stirred for an additional 3 minutes and vacuum filtered into a Buchner-funnel. The precipitate was washed with distilled water during filtration and dried on the filter paper by under air flow. Residual water was removed, where needed, by high-vacuum in a foil-encapsulated bottle affording 6.83 g (97%) of a yellow powder. The product disproportionates under UV-vis radiation and even in room temperature and should be used as fast as possible for follow-up synthesis.

Characteristics: $^1$H NMR (400 MHz, CDCl$_3$, ppm) δ 7.78-7.73 (m, 1H), 7.36-7.32 (m, 1H), 1.57 (s, 1H). $^{13}$C NMR (101 MHz, CDCl$_3$, ppm) δ 147.56, 146.30, 129.71, 125.46, 21.82. mp 87-92° C. (decomp.) (lit. 90° C. (decomp.)).

Example 7: Synthesis of 2-iodo-3-tosylpropanenitrile

Acrylonitrile (5 mmol, 0.33 mL) was dissolved in 20 mL propylene carbonate, 5% (V/V) water was added and the mixture stirred at 25° C. 1 eq. (1.41 g) of p-toluenesulfinyl iodide was used and the reaction maintained at 25° C. for 1 hour with visible light pulsed in 5 min intervals from a light source based on a 20 W LED die.

The reaction mixture was washed with sodium thiosulfate solution (10 w-%, 20 mL) and with a copious amount of water to precipitate the product as a white solid. The solid was collected in a Buchner-funnel, dried with excess air flow and residual water removed in high vacuum affording a white powder with an average isolated yield of 0.91 g (88%).

Characteristics: HRMS (ESI, m/z): [M+K]$^+$=373.9140, [M+MeCN+Na]$^+$=398.9670, [2M+Na]$^+$=692.8896. $^1$H NMR (400 MHz, CDCl$_3$, ppm) δ 7.86-7.81 (m, 2H), 7.44-7.40 (m, 2H), 4.62 (dd, J=11.0, 4.1 Hz, 1H), 3.90 (dd, J=14.5, 11.0 Hz, 1H), 3.69 (dd, J=14.5, 4.1 Hz, 1H), 2.48 (s, 3H). $^{13}$C NMR (101 MHz, CDCl$_3$, ppm) δ 146.45, 134.61, 130.49, 128.57, 116.84, 62.14, 21.82. mp 144-146° C. (decomp.) (lit. 150-152° C. (decomp.)).

Example 8: Elimination of Iodide to Form (E)-3-tosylacrylonitrile

The formation of 2-iodo-3-tosylpropanenitrile is performed according to Example 7. When the reaction between acrylonitrile and p-toluenesulfinyl iodide is complete, 2 eq. triethylamine is added and the mixture is stirred for 15 min. The reaction is quenched by the addition of aqueous Na$_2$S$_2$O$_3$ (10 mole-%, 25 mL). The organic phase is washed with water (3×30 mL) to precipitate the product. The solid was collected in a Buchner-funnel, dried with excess air flow and residual water removed in high vacuum affording an off-white powder with an average isolated yield of 80%.

The invention claimed is:
1. A process for a preparation of a compound of a general formula (I)

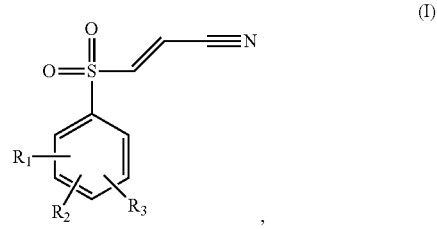

wherein R$_1$, R$_2$ and R$_3$ independently represent a hydrogen atom, a halogen atom, a hydroxy group, an amino group, an alkylamino group, an alkyl group, a hydroxyalkyl group, a haloalkyl group or an alkoxy group having 1 to 4 carbon atoms, or an acylamido group having 1 to 10 carbon atoms, said process comprising steps of:
i) mixing a sulfonyliodide and acrylonitrile in a solvent;
ii) initiating a radical reaction after step i) by irradiation with visible light;
iii) quenching the reaction; and
iv) adding a base to eliminate an iodide to form a desired product,
wherein the solvent is propylene carbonate and comprises 3% to 10% (V/V) water and the reaction is performed at a temperature of 25° C.-50° C.
2. The process according to claim 1, wherein, in Formula (I):
R$_1$ represents a methyl group, an ethyl group, a propyl group, a butyl group, a methoxy group, an ethoxy group, a propoxy group, an isopropoxy group, an n-butoxy group, or a tertiary butoxy group; and $R_2$ and $R_3$ represent independently a hydrogen atom, a methyl group, an ethyl group, a propyl group, a butyl group, a methoxy group, an ethoxy group, a propoxy group, an isopropoxy group, an n-butoxy group, a tertiary butoxy group.

3. The process according to claim 1, wherein, in Formula (I):
   $R_1$ represents a methyl group in the 4-position; and
   $R_2$ and $R_3$ represent hydrogen atoms.

4. The process according to claim 1, wherein the sulfonyliodide is formed in situ prior to step i).

5. The process according to claim 1, wherein the water content of said organic solvent is 5% (V/V).

6. The process according to claim 1, wherein the base used for elimination in step iii) is an organic or inorganic base.

7. The process according to claim 6, wherein the inorganic base is sodium bicarbonate, sodium hydroxide, sodium carbonate, or a mixture thereof.

8. The process according to claim 6, wherein the organic base is triethylamine, diethylamine, trimethylamine, sodium acetate, piperidine, pyridine, or a mixture thereof.

9. The process according to claim 1, wherein the reaction is performed in a batch or continuous flow reactor setup.

10. The process according to claim 7, wherein the inorganic base is sodium bicarbonate.

11. The process according to claim 8, wherein the organic base is triethylamine.

* * * * *